US011104914B2

(12) United States Patent
Wintermantel et al.

(10) Patent No.: US 11,104,914 B2
(45) Date of Patent: Aug. 31, 2021

(54) RNAI STRATEGIES FOR CONTROL OF WHITEFLY

(71) Applicant: The United States of America, as represented by the Secretary of Agriculture, Washington, DC (US)

(72) Inventors: William M. Wintermantel, Salinas, CA (US); Navneet Kaur, Salinas, CA (US); Wayne B. Hunter, Port Saint Lucie, FL (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 16/551,847

(22) Filed: Aug. 27, 2019

(65) Prior Publication Data

US 2020/0080105 A1 Mar. 12, 2020

Related U.S. Application Data

(60) Provisional application No. 62/724,127, filed on Aug. 29, 2018.

(51) Int. Cl.
*C12N 15/113* (2010.01)
*C12N 15/82* (2006.01)

(52) U.S. Cl.
CPC ........ *C12N 15/8286* (2013.01); *C12N 15/113* (2013.01); *C12N 2310/14* (2013.01)

(58) Field of Classification Search
CPC .............. C12N 15/8286; C12N 15/113; C12N 2310/14
See application file for complete search history.

(56) References Cited

U.S. PATENT DOCUMENTS

2007/0199100 A1 8/2007 Michaeli et al.

FOREIGN PATENT DOCUMENTS

WO 2016205445 A1 12/2016
WO 2017210764 A1 12/2017

OTHER PUBLICATIONS

Raza et al (PLoS One 11(4): e0153883. doi:10.1371/journal, 13 pages) (Year: 2016).*
GenBank Accession KX390870.1, retrieved from https://www.ncbi.nlm.nih.gov/nuccore/KX390870.1 on Aug. 16, 2020 (Year: 2017).*
Guo et al (Current Genomics, 2016, 17, 476-489) (Year: 2016).*
International Search Report for PCT/US2019/048504 dated Dec. 17, 2019.
NCBI, GenBank Accession No. XM_019061799.1, 'Predicted: Bemisia tabaci RNA exonuclease 4 (LOC109044215), mRNA', Nov. 9, 2016 See the whole document.
NCBI, GenBank Accession No. XM_019062335.1, 'Predicted: Bemisia tabaci flightin (LOC109044544), mRNA', Nov. 9, 2016 See the whole document.
NCBI, GenBank Accession No. XM_019048245.1, 'Predicted: Bemisia tabaci cadherin-23 (LOC109034869), mRNA', Nov. 9, 2016 See the whole document.
NCBI, GenBank Accession No. KC161217.1, 'Bemisia tabaci syntaxin 1A mRNA, complete cds', Apr. 22, 2013 See the whole document.
NCBI, GenBank Accession No. EF675187.1, 'Bemisia tabaci biotype B AChE1 (ace1) mRNA, ace1-R allele, complete cds', Sep. 22, 2008 See the whole document.
NCBI, GenBank Accession No. XM_019056709.1, 'Predicted: Bemisia tabaci lysosomal aspartic protease (LOC109040703), mRNA', Nov. 9, 2016 See the whole document.
NCBI, GenBank Accession No. XM_019042324.1, 'Predicted: Bemisia tabaci heat shock protein 83 (LOC109031045), mRNA', Nov. 9, 2016 See the whole document.

* cited by examiner

*Primary Examiner* — Richard A Schnizer
(74) *Attorney, Agent, or Firm* — John D. Fado; Mark D. McNemar

(57) ABSTRACT

The present disclosure provides compositions and methods utilizing double strand ribonucleic acid (dsRNA) to control insects, including whiteflies. More particularly, the present invention relates to several specific synthetic dsRNAs that induce RNA interference (RNAi) in the target insects and methods of delivering the dsRNAs to them, such as allowing feeding on plants treated with, or transgenically expressing, the dsRNAs.

7 Claims, 7 Drawing Sheets

Specification includes a Sequence Listing.

SEQUENCE LISTING

```
<160> NUMBER OF SEQ ID NOS: 10

<210> SEQ ID NO 1
<211> LENGTH: 474
<212> TYPE: RNA
```

<213> ORGANISM: Bemisia tabaci

<400> SEQUENCE: 1
atgtcggacc ccgatgcagc tgacgactgg ctatcagcag accccgagcc tgaaccagag 60
gctgcacccg cggaagccgc agaggccgca ccagaagccg cggctgccca aacagaagag 120
ctccctcctc cgccaagggc cagggacccc aacaggaaac tggtcttcag gcactgggtg 180
cgacccacat tcctgtcgta caagtacctg atggactaca ggaacaacta ctacgatgac 240
gtcatcgagt acctggacaa gaagaagcgc ggtctgcagc cggacatccc cgtgccacaa 300
acttggggtg agcggatgct gaggaccaac accagaggct tcccgacctc gaacgccgag 360
gaaggcttca agcacgacga acagctccta aataaaatca cctccgttgt acggtaccac 420
gcagagcaca ccaaggacta ctacagccgg aaatacaaag acatcctctt ataa 474

<210> SEQ ID NO 2
<211> LENGTH: 372
<212> TYPE: RNA
<213> ORGANISM: Bemisia tabaci

<400> SEQUENCE: 2
taggcagagt atccatcgta aactggaatg gagaatgtat ttacgataaa tatgtcaagc 60
ccatggaaaa agtcactgac tacagaacca gcgttagtgg cctgaaagct acagatctac 120
aaaatggtga ggattttact gttgttcaaa aagaggttgc aagtattctg aagggtaaaa 180
ttttagtcgg tcatgcctta accaatgatt ttaaagtatt gtttctgagt catccacgaa 240
gaaaaattcg agacacttca acatttcaca aatttcgtca ggcctgtggt aaaagaccaa 300
gtttgaaaaa attagtggca aaatttttac acaggaacat ccaagatggg gagcattgtt 360
caattgagga tg 372

<210> SEQ ID NO 3
<211> LENGTH: 778
<212> TYPE: RNA
<213> ORGANISM: Bemisia tabaci

<400> SEQUENCE: 3
gggagtaacg acactgtcta caggagtttc cgacctgcag ggtgtggcga tagaagcact 60
aatcacattt gtgctgcttt tagttgtcca gtccgtctgc gatgggaagc ggaccgacat 120
caaaggatct atcggcgttg cgataggatt gacagggaag cttgtccatc tggtgttggg 180
gacgactacc gtactcccgc aaggactccc ttccactgga actcctctaa gaatgcaggt 240
tttacgcagg ccagcaaacc atgggtaccg gtgaaccccg aatactaccg cactaatgtc 300
gaggtggaaa gaactttacg ctctaaatat cagacctctc acttggagaa tgatgaataa 360
ttattacaaa gctaccaatg attttcagtt catcaaaaaa aatatcaaga ctttgacaaa 420
ggagtttgaa tggtggcaga cgaaccggaa agtaaaattt atcaaagaca agaaaactta 480
caatatgttc cgatattatg ctccctcaaa tggaccaaga ccagaatctt atagagagga 540
ttatgaaatt gctcaaaccc ttccatctga aagtgagcgc acacgatggt atactcgtat 600
caagatttct catctagatg gttcatcaaa gacggtgcag gcaatggcac acttctggat 660
gttcacacgc ctagtataat acctgtcgac ttaaatgcat ttctccacaa gaatgctgtc 720
ttactaagcg aatggtggta catgatgggc gataagtacc gaggaaagta ctttaagg 778

<210> SEQ ID NO 4
<211> LENGTH: 655

<212> TYPE: RNA
<213> ORGANISM: Bemisia tabaci

<400> SEQUENCE: 4
gaggcatatg atttgggttt gccaactcca ctgactgcag atctggattt ggttgtctac 60
gttcgcagtg tgaacgatca tcagccgcag ttcttgattg atgaatttac tatcaatttt 120
actgagcatg agaaacctgg ttcagaacga gttaaacttg tagacacagt ggacagggat 180
cgggatgaaa tggatgaagt ggcagcagcc tcgatgccga tctgttacta cattgtagcc 240
ggaaacgatg acggatattt caaccttgag cctctaagtc atcaaattac ggttgtgcga 300
gaactagaca gggaagtggc tgactcccac gttctgataa tcaaagctct ggaggactgt 360
acccacgcac cgatgaagaa ggtggaattc tttgaccctc atgatgatac aaccctgaga 420
gttgtgataa atgtccttga tatcaacgat aaccctccga aattcatctc tcctgttttt 480
actggtggga taaccacaga gacagacttc ggaacagagt ttatgcaggt tcaggctatt 540
gatttagaca gcggtttaaa tgcaaaaatt gaatatagtt tgcatggtgg agttgaaatg 600
accttaacgg aagggcttga cattgttccg caaatgactc cgtttttggt tgacc 655

<210> SEQ ID NO 5
<211> LENGTH: 520
<212> TYPE: RNA
<213> ORGANISM: Bemisia tabaci

<400> SEQUENCE: 5
cagagtatct atattccaaa aggtgtaaac attccagctt taagcaaatc gcatgcatgg 60
gaattcaacc ccctgaatat caaaatcgga agtcacatca ctggtggaga cttgtacggt 120
attgtatttg aaagcttcga caggctccgt gaagttttgc agtgattttc tccccttaaa 180
tcgtcgaaaa tggccctcaa ttcaggtcta agtgcgaaac aagatgcgct cgagcatgta 240
atggcagtat cgagagactt ttcaagagga tcccaaactt taatgaagag tcgtctgaaa 300
ggagcacaga atggccacag tttactcaag aaaaaagcgg acgccctgca gatgcgattc 360
aggatgattc taggaaaaat tattgagacg acaaattagg cgtcattcca atcctagcag 420
atattctcag tgactctgtg aaagaaaaag ttacccgcat catcttggct gtattcagaa 480
acttaatcga aaaaccagaa gagccgaaca ttgcaaagga 520

<210> SEQ ID NO 6
<211> LENGTH: 239
<212> TYPE: RNA
<213> ORGANISM: Bemisia tabaci

<400> SEQUENCE: 6
ggaaacacag caggcaaaac aaactctagc agatattgaa gcaagacatg cggatattat 60
aaaattagaa aattctatac gagagttgca tgacatgttt atggatatgg ctatgcttgt 120
tgaaaaccag ggagaaatga ttgaccgtat cgaatatcat gtagaacatg cggtcgatta 180
tgttcaaact gcaacacaag atactaagaa agcattaaaa tatcagagta aagcgcggc 239

<210> SEQ ID NO 7
<211> LENGTH: 315
<212> TYPE: RNA
<213> ORGANISM: Citrullus lanatus

<400> SEQUENCE: 7
atgcgcctcc tcaccggcgc ctcctcctcc tttgtcttcg caccaatctc tgtcgtccca 60

-continued

```
tttgggccca atttcgtcct ggcggaaggc tacgacacaa aacgcgccgt ttcctgggtc    120

cacgcctgga ccattactga tgggatcatc acccacgtca aggaatatct caacacctct    180

gttactgtca agtgcttctc ctccgccgcc gacgggaact cgccttccgc atctccaccg    240

cctaactgcc agagtgtgtg gcagagcaag gtctggggag aatcggtggt gcctgctctt    300

gttttggctc tttag                                                     315
```

<210> SEQ ID NO 8
<211> LENGTH: 510
<212> TYPE: RNA
<213> ORGANISM: Bemisia tabaci

<400> SEQUENCE: 8

```
aaggcaaagt tcgaggcacc acgctcaccg cagcaacagg caaacaggtc gatgcctggc     60

tcggcatacc ttacgcacaa aaaccaatcg gggcactgcg gttccggcac ccgcggccga    120

tcgacaagtg ggaggggatc ctgaacgcga ccaagatgcc caactcgtgc acgcagatcg    180

tggatacggt cttcggcgac ttcgccggct cggccatgtg gaacccgaac acgcccatgt    240

ccgaggactg cctctacatc aacgtcatca ccccgaagcc ccggccccgc aacgccgccg    300

tcatggtctg gatcttcggc ggcggcttct acaccgggac ggccaccctc gacatctacg    360

actacaagat cctcgcctcc gaggagaacg tcatcctcgt ctccatgcag taccgcatca    420

cctgcctcgg cttcctctac ttcgacaccc aggacgtccc cggcaacgcg gggctcttcg    480

accagttgat ggccctccag tggatcagga                                     510
```

<210> SEQ ID NO 9
<211> LENGTH: 530
<212> TYPE: RNA
<213> ORGANISM: Bemisia tabaci

<400> SEQUENCE: 9

```
aactcctcct cagaatttta aggttgtttt cgatactgga tcctctaacc tttgggtgcc     60

ctccaaaaag tgtagcatca ccaacatagc atgtttgact cacagcaaat acaacagcaa    120

agcctcctcc acctatgtag ctaatggcac aaaattccat attgcttacg gatctggtag    180

tctcagtgga tttctctcta cagatactgt ttcgattgct gggttatcta ttgtaaacca    240

aacatttgca gaagctgtga cagaaccagg tctaattttt gtaatggcta agtttgatgg    300

tatcctagga cttggatatg atacaatctc tgttgatggt gttgttcctc ccatctacaa    360

aatgtaccag caaggtttaa ttgacgcacc agttttctca ttttatctaa acagaaacac    420

atcgactcag ccaggtggtg agattatttt tggtggctca gatagtgaaa agtacaaggg    480

tgacttcact tatgtacctg taaccaaaga aggatattgg cagttcacca               530
```

<210> SEQ ID NO 10
<211> LENGTH: 663
<212> TYPE: RNA
<213> ORGANISM: Bemisia tabaci

<400> SEQUENCE: 10

```
aagaagaata acatcaagtt gtacgtcaga cgagtattca tcatggacaa ttgcgaagat     60

ctcatacctg agtatctgaa ctttatcaag gggttgttg atagtgaaga tttgcctttg     120

aacatctctc gagaaatgtt acagcagaac aaaattttga aagtgattcg caaaaacttg    180

gtcaagaaat gtcttgaatt atttgaagag ttagcagaag acaaagaaaa ctaccaaaaa    240

ttctacgagc aatttagcaa gaacctgaaa ttgggcatgc acgaagatac gcaaaatagg    300
```

-continued

| | |
|---|---|
| aagaaattgt cagatttgct tcgttaccag acatctgcca gacttcagcc actggagacg | 360 |
| atgtctgctc atttaaagat tatgtagctc gtatgaaaga gaaccagaag catatctact | 420 |
| acatcactgg tgaaagcaaa gatcaagtag ctaactcctc atttgtcgag cgagtcaaga | 480 |
| aacgcggttt tgaagtaatc tacatgaccg aacccatcga tgaatatgta gtccagcaaa | 540 |
| tgaaagacta cgatggtaag aacctggtct cagtcacgaa agaaggatta gaactgcctg | 600 |
| aggacgaaga agaaaagaag aaatacgagg aagacaaagt taagttcgaa accctctgca | 660 |
| agg | 663 |

RNAI STRATEGIES FOR CONTROL OF WHITEFLY

CROSS-REFERENCE

The present application claims priority to U.S. Provisional Patent Application Ser. No. 62/724,127 filed Aug. 29, 2018, the content of which is expressly incorporated herein by reference.

BACKGROUND OF THE INVENTION

Field of Invention

The present disclosure provides compositions and methods utilizing double strand ribonucleic acid (dsRNA) to control the whitefly, *Bemisia tabaci*. More particularly, the present invention relates to several specific synthetic dsRNAs that induce RNA interference (RNAi) in the target insects and methods of delivering the dsRNAs to them.

Background

RNAi was first discovered in flower *petunia* when they learned that overexpressing chalcone synthase (CHS) in *petunia* resulted in unexpected white variegated petals instead of the normal deeper hue through co-suppression of the homologous CHS gene (Napoli et al, Plant Cell (1990) 2:279-89). In 1998, Fire and Mello discovered injecting double stranded ribonucleic acid (dsRNA) specific to the unc22 gene resulted in gene expression knockdown accompanied by a twitching movement in the worm, *Caenorhabditis elegans* (Fire et al, Nature (1998) 391:806-11). They called the phenomenon RNA interference.

The RNAi mechanism is present naturally in all eukaryotes and can be triggered by both exogenous and endogenous dsRNA that silences a gene with a sequence sharing high homology to the dsRNA. Whitefly, *Bemisia tabaci* MEAM1 (formerly known as biotype B and *Bemisia argentifolii*) possesses critical RNAi pathway genes, including DICER 1, DICER2, Ago1, and Ago2 (Chen et al., BMC Biol. (2016) 14:110), suggesting the potential for application of this technology in whitefly (Zhang et al, Mol. Immunol. (2017) 88:164-73).

RNAi has been used to control several different insects belonging to the orders Lepidoptera, Coleoptera, and Hemiptera, including the western corn rootworm *Diabrotica virgifera virgifera* (Baum et al, Nat. Biotechnol. (2007) 25:1322-26), whitefly *B. tabaci* MEAM1 (Thakur et al, PLoS One (2014) 9:e87235). RNAi studies have also been used to study gene function and their effects on mortality in whitefly, *B. tabaci*, MEAM1. RNAi was used to reduce expression of the immune system gene, BtToll in whitefly adults when the RNAi was acquired by feeding on solution containing dsRNA. This resulted in a significant reduction of the BtToll transcript accompanied by increased mortality when challenged with destruxin A, a secondary metabolite produced by entomopathogenic fungi, known for their high insecticidal activities against *B. tabaci* (Zhang et al., supra).

When long dsRNA molecules are directed against genes expressed in the midgut and salivary glands of the whitefly were injected into the body cavity of a whitefly, this resulted in a 70% reduction of target genes (Ghanim et al, Insect Biochem. Mol. Biol., (2007) 37:732-38). dsRNAs and small interfering ribonucleic acid (siRNAs) against actin, ADP/ATP translocase, α-tubulin, ribosomal protein L9 (RPL9), vATPase-A were administered to whitefly through the oral route, which caused 29-97% mortality along with significant reduction in the expression level of transcripts (Upadhay et al, J. Biosci., (2011) 36:153-61). Silencing of genes from the ecdysone synthesis and signaling pathway through leaf-mediated dsRNA feeding resulted in reduced survival and delayed development of whitefly nymphs (Luan et al, Insect Biochem. Mol. Biol., (2013) 43:740-6).

Whitefly is a serious agricultural pest that threatens economically important crops in developed and developing world such as tomato, cotton, and cassava (Navas-Castillo et al., Ann. Rev. Phytopathol., (2011) 49:219-48). The whitefly is a sap-sucking, phloem-feeding insect that transmits ~150 different types of viruses in addition to feeding on over 300 different species of plants (Lapidot & Polston, in "Biology and Epidemiology of *Bemisia*-vectored Viruses. *Bemisia*: Bionomics and Management of a Global Pest" (2010) Springer, NY, pp. 233-339). Current use of broad spectrum insecticides has led to creation of insecticide-resistant whitefly (Liang et al, Ecotoxicol. (2012) 21:1889-98; Wang et al, Pest Manag. Sci., (2010) 66:1360-66), thus reducing management options. Therefore, it is very important to develop alternative means to manage whitefly. RNAi holds promise as a technique to kill insects through disabling genes critical and specific to the species, without harming beneficial insects. Disclosed herein, we describe the development and testing of dsRNAs designed against novel gene targets in the whitefly, their efficacy and use.

SUMMARY OF THE INVENTION

The present disclosure provides multiple embodiments, including a double-stranded ribonucleic acid (dsRNA) comprising a first strand having a sequence with at least 95% identity to at least 19 consecutive nucleotides of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, or SEQ ID NO: 10 and a second strand complementary to the first strand. In some embodiments, the dsRNA has a first strand that is at least 99% or 100% identical to any one of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, or SEQ ID NO: 10. In some embodiments, the first strand comprises SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, or SEQ ID NO: 10. In some embodiments, the dsRNA is expressed in a plant cell. In other embodiments, the dsRNA is distributed throughout at least part of a living plant, such as a tomato plant, a cassava plant, or a cucurbits plant. In preferred embodiments, dsRNAs provided herein are capable of inducing ribonucleic acid interference (RNAi) when ingested by an insect, such as *Bemisia tabaci*.

The present disclosure also provides the embodiment of a DNA molecule comprising a promoter functional in a host cell and a heterologous DNA encoding a dsRNA comprising a first strand and a second strand, wherein the first strand comprises a sense region with at least 95% sequence identity a portion of at least 19 consecutive nucleotides of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, or SEQ ID NO: 10 and a second strand complementary to the first strand. In some embodiments, the host cell is a plant cell. Host cells, plant cells, plants and seeds containing these DNA and/or dsRNA molecules are also provided.

Further provided herein, is a method of inducing RNAi in an insect, comprising allowing the insect to feed on a plant comprising any of the dsRNAs provided herein such that the dsRNA is ingested by the insect, thereby inducing RNAi. In particular embodiments, such methods utilize a dsRNA with at least 95% sequence identity to a portion of at least 19 consecutive nucleotides of one or more of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, or SEQ ID NO: 10. In particular embodiments, the plant is a tomato plant, a cassava plant, or a curcurbits plant.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

FIG. 1A shows the results for a dsRNA targeting Acetylcholinesterase I (SEQ ID NO: 8). FIG. 1B shows the results for a dsRNA targeting Cathepsin D (SEQ ID NO: 9). FIG. 1C shows the results for a dsRNA concatemer targeting heat shock protein 90 (SEQ ID NO: 10). FIG. 1D shows the results for multiple dsRNAs targeting Flightin (SEQ ID NO: 1), locus Bta03986 (SEQ ID NO: 2), Aquaporin (SEQ ID NO: 3), Cadherin-23 (SEQ ID NO: 4), a concatemer targeting multiple ATP synthase components (SEQ ID NO: 5), and Syntaxin 1A (SEQ ID NO: 6).

DETAILED DESCRIPTION OF THE INVENTION

Figure 1A:
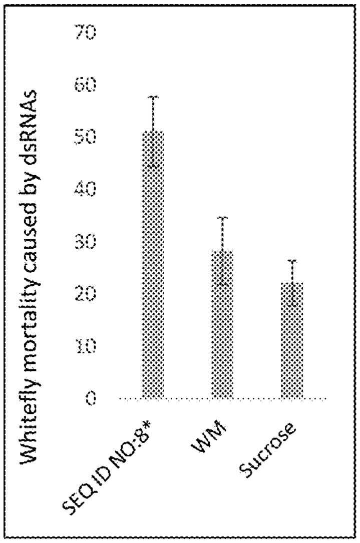
FIG. 1A-1D provide a graphical representation of whitefly mortality induced by different dsRNAs provided herein.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

RNA interference (RNAi) is a double stranded RNA (dsRNA) or small interfering RNA (siRNA) mediated gene-silencing mechanism that exists in animals and plants. RNAi has become a useful technology for functional gene regulation and provides a potential tool for development of bio-molecular pesticides. Described herein, molecular biopesticides detrimental to *Bemisia tabaci*, MEAM1 (biotype B), a plant-parasitic insect, were designed to target specific gene sequences. Although in vitro expression of a dsRNA by a transgenic plant is one mechanism to deliver the sequences of the present invention to target insects, any mechanism known in the art can be utilized, but preferably one that allows for ingestion.

Provided herein are methods and compositions for providing dsRNAs capable of controlling insect pests, such as whitefly, preferably by feeding. In some embodiments, dsRNA species are delivered to the insects via feeding on permanently or transiently transgenic plants expressing the dsRNAs. In other embodiments, the dsRNAs are delivered to the animals via feeding on plants that have taken up exogenous dsRNAs, or via feeding on alternate sources (e.g., baits) of the dsRNAs.

Definitions

As used in the specification and claims, use of the singular “a”, “an”, and “the” include plural references unless the context clearly dictates otherwise.

The terms isolated, purified, or biologically pure as used herein, refer to material that is substantially or essentially free from components that normally accompany the referenced material in its native state.

The term “about”, “approximately”, and similar terms are defined as plus or minus ten percent of a recited value. For example, about 1.0 g means from a range of 0.9 g to 1.1 g and all values within that range, whether specifically stated or not.

The term “gene” refers to a DNA sequence involved in producing a RNA or polypeptide or precursor thereof. The polypeptide or RNA can be encoded by a full-length coding sequence or by intron-interrupted portions of the coding sequence, such as exon sequences.

The term “oligonucleotide” refers to a molecule comprising a plurality of deoxyribonucleotides or ribonucleotides. Oligonucleotides may be generated in any manner known in the art, including chemical synthesis, DNA replication, reverse transcription, polymerase chain reaction, or a combination thereof. In one embodiment, the present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the “5' end” if its 5' phosphate is not linked to the 3' oxygen of a mononucleotide pentose ring and as the “3' end” if its 3' oxygen is not linked to a 5' phosphate of a subsequent mononucleotide pentose ring. As used herein, a nucleic acid sequence, even if internal to a larger oligonucleotide, also may be said to have 5' and 3' ends.

The term “a nucleic acid consisting essentially of”, and grammatical variations thereof, means nucleic acids that differ from a reference nucleic acid sequence by 20 or fewer nucleic acid residues and also perform the function of the reference nucleic acid sequence. Such variants include sequences that are shorter or longer than the reference nucleic acid sequence, have different residues at particular positions, or a combination thereof.

When two different, non-overlapping oligonucleotides anneal to different regions of the same linear complementary nucleic acid sequence, and the 3' end of one oligonucleotide points towards the 5' end of the other, the former may be called the “upstream” oligonucleotide and the latter the “downstream” oligonucleotide.

The term “primer” refers to an oligonucleotide, which is capable of acting as a point of initiation of synthesis when placed under conditions in which primer extension is initiated. An oligonucleotide “primer” may occur naturally, as in a purified restriction digest or may be produced synthetically.

A primer is selected to be “substantially complementary” to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

As used herein, “dsRNA” refers to double-stranded RNA that comprises a sense and an antisense portion of a selected target gene (or sequences with high sequence identity thereto so that gene silencing can occur), as well as any smaller double-stranded RNAs formed therefrom by RNAse or dicer activity. Such dsRNA can include portions of single-stranded RNA, but contains at least 19 nucleotides double-stranded RNA. In one embodiment of the invention, a dsRNA comprises a hairpin RNA which contains a loop or spacer sequence between the sense and antisense sequences of the gene targeted, preferably such hairpin RNA spacer region contains an intron, particularly the rolA gene intron (Pandolfini et al., 2003, BioMedCentral (BMC) Biotechnology 3:7 (www.biomedcentral.com/1472-6750/3/7)), the dual orientation introns from pHellsgate 11 or 12 (see, WO 02/059294 and SEQ ID NO: 25 and 15 therein) or the pdk intron (Flaveria trinervia pyruvate orthophosphate dikinase intron 2; see WO99/53050).

Included in this definition are “siRNAs” or small interfering (double-stranded) RNA molecules of 16-30 bp, 19-28 bp, or 21-26 bp, e.g., such as the RNA forms that can be created by RNAseIII or dicer activity from longer dsRNA. siRNAs as used herein include any double-stranded RNA of 19 to 26, or 21 to 24 base pairs that can interfere with gene expression when present in a cell wherein such gene is expressed. siRNA can be synthetically made, expressed and secreted directly from a transformed cell or can be generated from a longer dsRNA by enzymatic activity. These siRNAs can be blunt-ended or can have overlapping ends. Also, modified microRNAs comprising a portion of a target gene and its complementary sequence are included herein as dsRNAs.

Sequences or parts of sequences which have “high sequence identity”, as used herein, refers to the number of positions with identical nucleotides divided by the number of nucleotides in the shorter of the sequences, being higher than 95%, higher than 96%, higher than 97%, higher than 98%, higher than 99%, or between 96% and 100%. A target gene, or at least a part thereof, as used herein, preferably has high sequence identity to the dsRNA of the invention in order for efficient gene silencing to take place in the target pest. Identity in sequence of the dsRNA or siRNA with a part of the target gene RNA is included in the current invention but is not necessary.

For the purpose of this disclosure, the “sequence identity” of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

For the purpose of the invention, the “complement of a nucleotide sequence X” is the nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff’s rules (A< >T; G< >C; A< >U) and reading in the 5' to 3' direction, i.e., in opposite direction of the represented nucleotide sequence.

A dsRNA “targeting” a gene, mRNA or protein, as used herein, refers to a dsRNA that is designed to be identical to, or have high sequence identity to, one or more mRNAs endogenous to the target organism (the target genes), and as such is designed to silence such gene upon application to such organisms (e.g., whiteflies). One dsRNA construct can target one or several homologous target genes in one pest, or one or several homologous target genes in different pests which can feed on the same host plant. One of skill in the art will recognize that multiple currently-known genes, as well as other currently unknown or uncharacterized genes can be targeted by applying the teachings herein.

“Insecticidal activity” of a dsRNA, as used herein, refers to the capacity to obtain mortality in a target insect when such dsRNA is fed to the insect, which mortality is significantly higher than a negative control (using a non-relevant dsRNA or buffer).

“Insect control” using a dsRNA, as used herein, refers to the capacity to inhibit insect development, fertility, inhibition of pheromone production, or growth in such a manner that the insect population provides less damage to a plant, produces fewer offspring, are less fit or are more susceptible to predator attack, or that insects are even deterred from feeding on such plant.

The term “corresponds to” as used herein means a polynucleotide sequence homologous to all or a portion of a reference polynucleotide sequence, or a polypeptide sequence that is identical to a reference polypeptide sequence. In contradistinction, the term “complementary to” is used herein to mean that the complementary sequence is homologous to all or a portion of a reference polynucleotide sequence. For example, the nucleotide sequence “TATAC” corresponds to a reference sequence “TATAC” and is complementary to a reference sequence “GTATA”. An “RNA from” of a DNA sequence, as used herein is the RNA sequence of said DNA, so the same sequence but wherein the T nucleotide is replaced by a U nucleotide.

The term “plant” includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seeds (including embryo, endosperm, and seed coat) and fruit (the mature ovary), plant tissue (e.g., vascular tissue, ground tissue, and the like) and cells (e.g., guard cells, egg cells, trichomes and the like). Any plant on which whiteflies feed are included in this invention.

An “effective amount” is an amount sufficient to effect desired beneficial or deleterious results. An effective amount can be administered in one or more administrations. In terms of treatment, an “effective amount” is that amount sufficient to make the target pest non-functional by causing an adverse effect on that pest, including (but not limited to) physiological damage to the pest; inhibition or modulation of pest growth; inhibition or modulation of pest reproduction; or death of the pest. In one embodiment of the invention, a dsRNA containing solution is fed to a target pest, wherein critical developmental and/or reproductive functions of the insect are disrupted as a result of ingestion.

General Overview

Double-stranded RNA (dsRNA) mediated gene silencing, also known as RNA interference (RNAi), is a breakthrough technology for functional genomic studies providing a potential tool for management of agricultural and horticultural pests. Since the inception of RNAi numerous studies have documented successful introduction of synthetic dsRNA or siRNA into the organism that triggers a highly efficient gene silencing through degradation of endogenous RNA homologous to the presented dsRNA/siRNA. One focus of the present invention is providing for RNAi-mediated control of insects, namely the whitefly, *Bemisia tabaci*, MEAM1 (biotype B).

RNAi technology can serve as a viable tool for control and management of this voracious pest, however, the major obstacle to utilizing RNAi approaches is the challenge of delivery of effective amounts of dsRNA to the target insects. Mechanical microinjection of dsRNAs and soaking dsRNA(s)-containing liquids are both methods that have been successfully utilized for eliciting effective RNAi response in laboratory studies of some species. These techniques, however, are impracticable in an agricultural setting. One approach that can be used to induce RNAi via feeding by the insect(s) on plants containing dsRNA(s) that control the insect by, for example, increasing mortality, decreasing fertility, or otherwise decreasing the damage done to target plants. One method to introduce dsRNA(s) into plants is to construct transgenic plants expressing dsRNA species targeting insects such as whitefly that are important to that particular plant (see, e.g., PCT Appl. No. WO2001037654). Alternately, dsRNAs can be applied physically to a target plant, allowing for uptake of the dsRNA and distribution throughout the plant (Hunter et al., Soc. Southwestern Entomologists (2012) 37(1):85-87).

To be relevant for agricultural or horticultural control, delivery of dsRNA to target pests should be economical, efficient and advantageous. dsRNA delivered through ingestion of its solution directly (Baum et al., supra), by feeding bacteria expressing dsRNA (Timmons and Fire, Nature, (1998) 395:854), or via a dsRNA-containing diet are other possible strategies for inducing RNAi as an agricultural pest control methodology. The compositions and methodologies disclosed herein can utilize any of these routes, as well as any other route known in the art.

Double-Stranded RNA and RNA Interference

Since its inception, RNAi has proved to be a potent tool to study gene function and regulation. With the advent of bioinformatics coupled with next-generation high throughput sequencing has unveiled an array of transcriptomic data available for a wide range of species at different stages of development and tissues. To attain an effective RNAi response in the biocontrol of pests, an accurate and precise mode of dsRNA delivery, efficient uptake and dsRNA stability are of utmost consideration.

Preferably, the dsRNAs to be used in this invention target at least one insect gene portion of at least 19 consecutive nucleotides occurring in identical sequence or with high sequence identity in the one or more target insects. In preferred embodiments of this invention, such dsRNAs do not silence genes of a plant host, or of other non-target animals, such as beneficial insects (e.g., pollinators), pest predators or animals such as reptiles, amphibians, birds, or mammals. Levels of identity between sequences of interest can be analyzed in available databases, e.g., by a BLAST search (see also www.ncbi.nlm.nih.gov/BLAST) or by hybridization with existing DNA libraries of representative non-target organisms.

As used herein, nucleotide sequences of RNA molecules can be identified by reference to DNA nucleotide sequences of the sequence listing. However, the person skilled in the art will understand whether RNA or DNA is meant depending on the context. Furthermore, the nucleotide sequence is identical between the types of polynucleotides except that the T-base is replaced by uracil (U) in RNA molecules.

In some embodiments, the length of the first (e.g., sense) and second (e.g., antisense) nucleotide sequences of the dsRNA molecules of the invention can vary from about 10 nucleotides (nt) up to a length equaling the length in nucleotides of the transcript of the target gene. The first and second sequences can be referred to as first and second strands. Additionally, it is understood that either the first or second sequence can be the sense or antisense strand. The length of the first or second nucleotide sequence of the dsRNA of the invention can be at least 15 nt, or at least about 20 nt, or at least about 50 nt, or at least about 100 nt, or at least about 150 nt, or at least about 200 nt, or at least about 400 nt, or at least about 500 nt. If not all nucleotides in a target gene sequence are known, it is preferred to use such portion for which the sequence is known and which meets other beneficial requirements of the invention.

It will be appreciated that the longer the total length of the first (sense) nucleotide sequence in the dsRNA of the invention is, the less stringent the requirements for sequence identity between the total sense nucleotide sequence and the corresponding sequence in the target gene becomes. The total first nucleotide sequence can have a sequence identity of at least about 75% with the corresponding target sequence, but higher sequence identity can also be used such as at least about 80%, at least about 85%, at least about 90%, at least about 95%, about 100%. The first nucleotide sequence can also be identical to the corresponding part of the target gene. However, it is preferred that the first nucleotide sequence includes a sequence of 19 or 20, or about 19 or about 20 consecutive nucleotides, or even of about 50 consecutive nucleotides, or about consecutive 100 nucleotides, or about 150 consecutive nucleotides with only one mismatch, preferably with 100% sequence identity, to the corresponding part of the target gene. For calculating the sequence identity and designing the corresponding first nucleotide sequence, the number of gaps should be minimized, particularly for the shorter sense sequences.

The length of the second (antisense) nucleotide sequence in the dsRNA of the invention is largely determined by the length of the first (sense) nucleotide sequence, and may correspond to the length of the latter sequence. However, it is possible to use an antisense sequence which differs in length by about 10% without any difficulties. Similarly, the nucleotide sequence of the antisense region is largely determined by the nucleotide sequence of the sense region, and may be identical to the complement of the nucleotide sequence of the sense region. Particularly with longer antisense regions, it is however possible to use antisense sequences with lower sequence identity to the complement of the sense nucleotide sequence, such as at least about 75% sequence identity, or least about 80%, or at least about 85%, more particularly with at least about 90% sequence identity, or at least about 95% sequence to the complement of the sense nucleotide sequence. Nevertheless, it is preferred that the antisense nucleotide sequence includes a sequence of between 16-26 nucleotides, preferably between 19-23 nucleotides, or about 19, about 20, about 21, about 22, or about 23 consecutive nucleotides, although longer stretches of consecutive nucleotides such as about 50 nucleotides, or about 100 nucleotides, or about 150 nucleotides with no more than one mismatch, preferably with 100% sequence identity, to the complement of a corresponding part of the sense nucleotide sequence can also be used. Again, the number of gaps should be minimized, particularly for the shorter (19 to 50 nucleotides) antisense sequences.

In one embodiment of the invention, a dsRNA molecule may further comprise one or more regions having at least 94%, at least 95%, at least 96%, at least 97%, at least 98%, or at least 99%, sequence identity to regions of at least 19 consecutive nucleotides from the sense nucleotide sequence of the target gene, different from the at least 19 consecutive nucleotides as defined in the first region, and one or more regions having at least 94%, at least 95%, at least 96%, at least 97%, at least 98%, or at least 99%, sequence identity to at least 19 consecutive nucleotides from the complement of the sense nucleotide sequence of the target gene, different from the at least 19 consecutive nucleotides as defined in the second region, wherein these additional regions can base-pair amongst themselves.

Transgenic Plants and Plant Cells

One embodiment of the present invention provides a plant or cell comprising one or more inhibitory dsRNAs specific for one or more mRNAs of one or more *Bemisia tabaci*, MEAM1 (biotype B) genes. Inhibitory RNAs specific for one or more mRNAs means that the inhibitory RNA down-regulates the expression, or translation, of a specific mRNA. The inhibitory RNA can be single- or double-stranded or a combination thereof. For example, the present disclosure provides dsRNAs that down regulate expression, or translation, of one or more target genes when the one or more inhibitory RNAs are absorbed or ingested by a target insect (e.g., *Bemisia tabaci*, MEAM1 (biotype B)).

Another embodiment provides a transgenic plant that comprises inhibitory RNA that down regulates 3, 4, 5, 6, 7, 8, 9, 10, 11, 12, 13, 14, 15, 16, 17, 18, 19, 20, or more whitefly genes. Thus, the present disclosure provides transgenic plants and transgenic plant material that are resistant to disease caused by *Bemisia tabaci*, MEAM1 (biotype B).

Another embodiment provides a transgenic plant or transgenic cell containing or expressing one or more inhibitory nucleic acids specific for at least a portion of a nucleic acid encoding one or more *B. tabaci*, MEAM1 (biotype B) genes. The inhibitory nucleic acid is typically a small inhibitory RNA or microRNA that is specific for mRNA encoding a *B. tabaci* gene involved in growth, general health, fecundity, or reproduction. In some instances, the function of the target gene (or the protein encoded by the gene) is not known.

It will be appreciated by one of skill in the art that an inhibitory nucleic acid can be RNA, DNA, or a combination thereof. Additionally, the inhibitory nucleic acid can be single or multi-stranded and can be anti-sense or enzymatic. In one embodiment, an inhibitory nucleic acid interferes with, inhibits, or reduces the translation of a target mRNA. For example, an inhibitory nucleic acid can bind to a target mRNA and induce or promote the degradation of the target mRNA or physically prevent the cellular translational machinery from translating the target mRNA into a functional protein.

In some embodiments, a dsRNA encoding sequence, encoding a dsRNA targeting any of the genes (or portions of genes) disclosed herein, can be stably or transiently inserted in a conventional manner into the genome of a single plant cell, and the so-transformed plant cell can be used in a conventional manner to produce a transformed (i.e., transgenic) plant that has increased insect resistance. In this regard, a disarmed Ti-plasmid, containing the dsRNA chimeric gene, in *Agrobacterium tumefaciens* can be used to transform the plant cell, and thereafter, a transformed plant can be regenerated from the transformed plant cell using the procedures described in the art, for example, in EP 0116718, EP 0270822, PCT publication WO 84/02913 and published European Patent application ("EP") 0242246. Preferred Ti-plasmid vectors each contain the dsRNA chimeric gene between the border sequences, or at least located to the left of the right border sequence, of the T-DNA of the Ti-plasmid. Such transgenic plants can be transiently transgenic (e.g., "agroinfiltrated"). Of course, other types of vectors can be used to transform the plant cell, using procedures such as direct gene transfer (as described, for example in EP 0233247), pollen mediated transformation (as described, for example in EP 0270356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm et al., Bio/Technology (1990) 8, 833-839); Gordon-Kamm et al., The Plant Cell, (1990) 2, 603-618) and rice (Shimamoto et al., Nature, (1989) 338, 274-276; Datta et al., Bio/Technology, (1990) 8, 736-740) and the method for transforming monocots generally (PCT publication WO 92/09696). For cotton transformation, the method described in PCT patent publication WO 00/71733 can be used. For soybean transformation, reference is made to methods known in the art, e.g., Hinchee et al. (Bio/Technology, (1988) 6, 915) and Christou et al. (Trends Biotech, (1990) 8, 145) or the method of WO 00/42207.

The resulting transgenic plant can be used in a conventional plant breeding scheme to produce more transgenic plants with the same characteristics, or to introduce the dsRNA chimeric gene in other varieties of the same or related plant species. Seeds, which are obtained from the transformed plants, contain the dsRNA encoding sequence as a stable genomic insert. Plants comprising a dsRNA in accordance with the invention include plants comprising, or derived from, root stocks of plants comprising the dsRNA encoding sequence of the invention, e.g., crop species or ornamental plants. Hence, any non-transgenic grafted plant parts inserted on a transformed plant or plant part are included in the invention since the RNA interference signal is transported to these grafted parts and any insects feeding on such grafted plant are similarly affected by the dsRNA or siRNA of the invention.

A DNA encoding a dsRNA is typically inserted in a plant cell genome so that this DNA is downstream (i.e., 3') of, and operably linked to, a plant-expressible promoter which can direct expression in plant cells. This is preferably accomplished by inserting a dsRNA encoding sequence into the plant cell genome, particularly in the nuclear or plastid (e.g., chloroplast) genome. Also, in a dsRNA encoding sequence of the invention a nuclear localization signal can be added as described in published US patent application 20030180945.

A 'plant-expressible promoter' as used herein refers to a promoter that ensures expression of a dsRNA of the invention in a plant cell. Examples of promoters directing constitutive expression in plants are known in the art and include: the strong constitutive 35S promoters (the "35S promoters") of the cauliflower mosaic virus (CaMV), e.g., of isolates CM 1841 (Gardner et al., Nucleic Acids Res, (1981) 9, 2871-2887), CabbB-S (Franck et al., Cell (1980) 21, 285-294) and CabbB-JI (Hull and Howell, Virology, (1987) 86, 482-493); promoters from the ubiquitin family (e.g., the maize ubiquitin promoter of Christensen et al., Plant Mol Biol, (1992) 18, 675-689), the gos2 promoter (de Pater et al., The Plant J (1992) 2, 834-844), the emu promoter (Last et al., Theor Appl Genet, (1990) 81, 581-588), actin promoters such as the promoter described by An et al. (The Plant J, (1996) 10, 107), the rice actin promoter described by Zhang et al. (The Plant Cell, (1991) 3, 1155-1165); promoters of the Cassava vein mosaic virus (WO 97/48819, Verdaguer et al. (Plant Mol Biol, (1998) 37, 1055-1067), the pPLEX series of promoters from Subterranean Clover Stunt Virus (WO 96/06932, particularly the S4 or S7 promoter), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., EMBO J, (1984) 3, 2723-2730).

Alternatively, a plant-expressible promoter can be a tissue-specific promoter, i.e., a promoter directing a higher level of expression in some cells or tissues of the plant, e.g., in green tissues (such as the promoter of the PEP carboxylase). The plant PEP carboxylase promoter (Pathirana et al., Plant J, (1997) 12:293-304) has been described to be a strong promoter for expression in vascular tissue and is useful in one embodiment of the current invention. Alternatively, a plant-expressible promoter can also be a wound-inducible promoter, such as the promoter of the pea cell wall invertase gene (Zhang et al., Plant Physiol, (1996) 112:1111-1117). A 'wound-inducible' promoter as used herein means that upon wounding of the plant, either mechanically or by pest feeding, expression of the coding sequence under control of the promoter is significantly increased in such plant. These plant-expressible promoters can be combined with enhancer elements, they can be combined with minimal promoter elements, or can comprise repeated elements to ensure the expression profile desired.

Elements which can be used to increase expression in plant cells can be: an intron at the 5' end or 3' end of the chimeric gene, or in the coding sequence of the chimeric dsRNA encoding sequence (such as between the region encoding the sense and antisense portion of the dsRNA), e.g., the hsp70 intron, besides promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence.

A dsRNA encoding sequence of the present invention can be inserted in a plant genome so that the inserted gene part is upstream (i.e., 5') of suitable 3' end transcription regulation signals (i.e., transcript formation and polyadenylation signals). This is preferably accomplished by inserting the dsRNA chimeric gene in the plant cell genome. Preferred polyadenylation and transcript formation signals include those of the nopaline synthase gene (Depicker et al., J. Molec Appl Gen, (1982) 1, 561-573), the octopine synthase gene (Gielen et al., EMBO J, (1984) 3:835-845), the SCSV or the Malic enzyme terminators (Schunmann et al., Plant Funct Biol, (2003) 30:453-460), and the T-DNA gene 7 (Velten and Schell, Nucleic Acids Res, (1985) 13, 6981-6998), which act as 3'-untranslated DNA sequences in transformed plant cells.

In some instances, a dsRNA encoding sequence of the present invention can optionally be inserted in a plant genome as a hybrid gene, containing several dsRNA regions which target different genes. For example, a dsRNA chimeric gene can have dsRNA regions targeting 2, 3, 4, 5, 6, 7, 8, 9, 10, 11, 12, 13, 14, 15, 16, 17, 18, 19, 20 or more genes from *B. tabaci*, an additional pest species, or a combination thereof. In some embodiments, a dsRNA chimeric gene of the present invention can contain several dsRNA regions which target different portions of the same gene, or target different alleles of the same gene. Also, it is convenient to include in the transforming DNA of the invention also a selectable or scorable marker gene, such as the bar, epsps or the neo gene, so that transformed plants can easily be selected by application of glufosinate, glyphosate or kanamycin, respectively, as is well known in the art. Advantageously, the plants or seeds of the invention also comprise a glufosinate or glyphosate tolerance gene besides the dsRNA chimeric gene of the invention, so that plants can be selected using application of the relevant herbicide (glufosinate or glyphosate).

Non-Transgenic dsRNA Delivery

Although plant delivery of a dsRNA is an embodiment of this invention, application of the dsRNA(s) of the invention can be done in several ways, and need not be by way of a plant expressing a dsRNA. Any method of delivery of dsRNA not contained in a plant cell is included herein, e.g., in vitro or in vivo produced dsRNA applied to an artificial diet or feed, dsRNA applied to a plant, or microbially- or yeast-expressed dsRNA. dsRNA(s) can be applied on plants on which a whitefly feeds by spraying a solution of dsRNA of the invention, or microbial cells comprising the dsRNA of the present disclosure. dsRNA species of the present invention can be applied on plants by spraying a culture, culture extract, culture supernatant, or a combination thereof, where the sprayed material comprises a microbe-expressed dsRNA. Thus, the present invention includes microbes comprising genetic elements allowing for the expression of any of the dsRNA species described herein. Application to a plant of a solution containing a dsRNA of the present invention can include any application methodology known in the art, including foliar spray, trunk or stem injection, or root soaking.

In particular embodiments, the present invention provides a composition having an inhibitory nucleic acid specific for an mRNA or fragment thereof represented by one or more of SEQ ID NO: 1, 2, 3, 4, 5 and 6 or a fragment or homologue thereof. Typically, dsRNAs of the present invention are provided to a target pest in an amount sufficient to inhibit production of the polypeptide encoded by one or more of the full-length genes targeted by SEQ ID NO: 1, 2, 3, 4, 5 and 6 or homologs and alleles thereof. For example, when whiteflies, or another target pest, are feeding on a plant or cell expressing, or containing, or coated with an inhibitory nucleic acid, the insect ingests a sufficient level of dsRNA comprising 19 or more consecutive nucleotides of SEQ ID NO: 1, 2, 3, 4, 5 and 6 to result in a phenotypic effect.

In embodiments where a dsRNA is applied to a plant, a biopesticide composition of the present invention can contain one or more phagostimulants, pesticides, fungicides, or combinations thereof. The composition can be formulated to be coated on a plant, plant part, or seed. In certain aspects the inhibitory nucleic acid is combined with one or more excipients, buffering agents, carriers, etc. excipients, buffering agents, and carriers are well known in the art. The coating can be formulated as a spray or dip so that the inhibitory nucleic acids remain on the plant material and remain able to inhibit target protein expression in the target insect as the plant matures and develops. For example, the seed of a plant can be coated with a composition comprising an amount of one or more of the disclosed inhibitory nucleic acids effective to inhibit or reduce predation in the plant in combination with an excipient.

Compositions of the invention disclosed herein can be applied to soil, fruits, vegetables, crops, and any other desired target using any delivery methodology known to those of skill in the art. For example, the compositions can be applied to the desired locale via methods and forms including, but not limited to, root soaking, shank injection, sprays, granules, flood/furrow methods, sprinklers, fumigation, root soaking and drip irrigation. In embodiments of the invention where the compositions are sprayed onto a desired locale, the compositions can be delivered as a liquid, liquid suspension, emulsion, microemulsion or powder. In other embodiments, granules or microcapsules containing dsRNA(s) can be used to deliver the compositions of the invention to the plants.

The compositions of the present invention can be applied to plants and/or crops by any convenient method, for example, by using a fixed application system such as a center pivot irrigation system. Preferably, application to fields of plants and/or crops is made by air spraying, i.e., from an airplane or helicopter, or by land spraying. For example, land spraying can be carried out by using a high flotation applicator equipped with a boom, by a back-pack sprayer or by nurse trucks or tanks. One of skill in the art will recognize that these application methodologies are provided for example and that any applicable methods known in the art or developed in the future can be utilized.

In some embodiments, dsRNAs of the present invention are applied to a plant in solutions having concentrations of dsRNA ranging from 10-500 μg/mL, and preferably between 40-200 μg/mL. Any specific concentration of dsRNA encompassed within these ranges is contemplated herein. Application of the dsRNAs of the present invention can also be applied such that 1 ng-20 μg of dsRNA is applied to a plant, or a specific surface on the plant, such as a leaf, stem, flower, fruit, root or seed. The present disclosure contemplates the use of concentrations outside these ranges as well, and determining a functional concentration is well within the capabilities of the skilled artisan.

dsRNAs of the present invention can be applied to plants a single time, or at multiple times, as needed to affect the target insect. In some instances, subsequent dsRNA application can occur 1, 2, 3, 4, 5, 6, 7, 8, 9, 10, 11, 12, 13, 14, 15, 16, 17, 18, 19, 20, or more days or weeks following an initial application. Studies have shown that delivery of dsRNA at a dosage of 5 ug/leaf to leaves of vegetable crop test plants (potato) can remain viable with no loss of infectivity by 28 days post treatment (Miguel & Scott, Pest Manag. Sci., (2016); 72: 801-809). Furthermore, once dsRNA applied to leaves dried, it was not readily removed. dsRNA targeting actin was applied to leaves of test plants, dried, then soaked in water for 1 hour, with no significant loss of biological activity (Miguel and Scott, 2016).

dsRNA Species

We developed and tested the efficacy of several different dsRNAs designed against gene(s) that are critical to the life cycle of whitefly. These are listed in Table 1.

TABLE 1

| dsRNA constructs | | |
|---|---|---|
| Whitefly gene target(s) | Sequence | SEQ ID NO: |
| Flightin (Bta04605) | ATGTCGGACCCCGATGCAGCTGACGACTGGCTATCAGCAG<br>ACCCCGAGCCTGAACCAGAGGCTGCACCCGCGGAAGCCGC<br>AGAGGCCGCACCAGAAGCCGCGGCTGCCCAAACAGAAGAG<br>CTCCCTCCTCCGCCAAGGGCCAGGGACCCCAACAGGAAAC<br>TGGTCTTCAGGCACTGGGTGCGACCCACATTCCTGTCGTA<br>CAAGTACCTGATGGACTACAGGAACAACTACTACGATGAC<br>GTCATCGAGTACCTGGACAAGAAGAAGCGCGGTCTGCAGC<br>CGGACATCCCCGTGCCACAAACTTGGGGTGAGCGGATGCT<br>GAGGACCAACACCAGAGGCTTCCCGACCTCGAACGCCGAG<br>GAAGGCTTCAAGCACGACGAACAGCTCCTAAATAAAATCA<br>CCTCCGTTGTACGGTACCACGCAGAGCACACCAAGGACTA<br>CTACAGCCGGAAATACAAAGACATCCTCTTATAA | 1 |
| Bta03986 | TAGGCAGAGTATCCATCGTAAACTGGAATGGAGAATGTAT<br>TTACGATAAATATGTCAAGCCCATGGAAAAAGTCACTGAC<br>TACAGAACCAGCGTTAGTGGCCTGAAAGCTACAGATCTAC<br>AAAATGGTGAGGATTTTACTGTTGTTCAAAAAGAGGTTGC<br>AAGTATTCTGAAGGGTAAAATTTTAGTCGGTCATGCCTTA<br>ACCAATGATTTTAAAGTATTGTTTCTGAGTCATCCACGAA<br>GAAAAATTCGAGACACTTCAACATTTCACAAATTTCGTCA<br>GGCCTGTGGTAAAAGACCAAGTTTGAAAAAATTAGTGGCA<br>AAATTTTTACACAGGAACATCCAAGATGGGGAGCATTGTT<br>CAATTGAGGATG | 2 |
| Aquaporin (Bta01973)-alpha-glucosidase (Bta11979)-trehalase (Bta12860) | GGGAGTAACGACACTGTCTACAGGAGTTTCCGACCTGCAG<br>GGTGTGGCGATAGAAGCACTAATCACATTTGTGCTGCTTT<br>TAGTTGTCCAGTCCGTCTGCGATGGGAAGCGGACCGACAT<br>CAAAGGATCTATCGGCGTTGCGATAGGATTGACAGGGAAG<br>CTTGTCCATCTGGTGTTGGGGACGACTACCGTACTCCCGC<br>AAGGACTCCCTTCCACTGGAACTCCTCTAAGAATGCAGGT<br>TTTACGCAGGCCAGCAAACCATGGGTACCGGTGAACCCCG<br>AATACTACCGCACTAATGTCGAGGTGGAAAGAACTTTACG<br>CTCTAAATATCAGACCTCTCACTTGGAGAATGATGAATAA<br>TTATTACAAAGCTACCAATGATTTTCAGTTCATCAAAAAA<br>AATATCAAGACTTTGACAAAGGAGTTTGAATGGTGGCAGA<br>CGAACCGGAAAGTAAAATTTATCAAAGACAAGAAAACTTA<br>CAATATGTTCCGATATTATGCTCCCTCAAATGGACCAAGA<br>CCAGAATCTTATAGAGAGGATTATGAAATTGCTCAAACCC<br>TTCCATCTGAAAGTGAGCGCACACGATGGTATACTCGTAT<br>CAAGATTTCTCATCTAGATGGTTCATCAAAGACGGTGCAG<br>GCAATGGCACACTTCTGGATGTTCACACGCCTAGTATAAT<br>ACCTGTCGACTTAAATGCATTTCTCCACAAGAATGCTGTC<br>TTACTAAGCGAATGGTGGTACATGATGGGCGATAAGTACC<br>GAGGAAAGTACTTTAAGG | 3 |
| Cadherin-23 (Bta02325) | GAGGCATATGATTTGGGTTTGCCAACTCCACTGACTGCAG<br>ATCTGGATTTGGTTGTCTACGTTCGCAGTGTGAACGATCA<br>TCAGCCGCAGTTCTTGATTGATGAATTTACTATCAATTTT<br>ACTGAGCATGAGAAACCTGGTTCAGAACGAGTTAAACTTG<br>TAGACACAGTGGACAGGGATCGGGATGAAATGGATGAAGT<br>GGCAGCAGCCTCGATGCCGATCTGTTACTACATTGTAGCC<br>GGAAACGATGACGGATATTTCAACCTTGAGCCTCTAAGTC<br>ATCAAATTACGGTTGTGCGAGAACTAGACAGGGAAGTGGC<br>TGACTCCCACGTTCTGATAATCAAAGCTCTGGAGGACTGT<br>ACCCACGCACCGATGAAGAAGGTGGAATTCTTTGACCCTC<br>ATGATGATACAACCCTGAGAGTTGTGATAAATGTCCTTGA<br>TATCAACGATAACCCTCCGAAATTCATCTCTCCTGTTTTT<br>ACTGGTGGGATAACCACAGAGACAGACTTCGGAACAGAGT<br>TTATGCAGGTTCAGGCTATTGATTTAGACAGCGGTTTAAA<br>TGCAAAAATTGAATATAGTTTGCATGGTGGAGTTGAAATG<br>ACCTTAACGGAAGGGCTTGACATTGTTCCGCAAATGACTC<br>CGTTTTTGGTTGACC | 4 |
| NKcat V-type ATP synthase alpha chain (Bta08447)-V-type ATP synthase beta | CAGAGTATCTATATTCCAAAAGGTGTAAACATTCCAGCTT<br>TAAGCAAATCGCATGCATGGGAATTCAACCCCCTGAATAT<br>CAAAATCGGAAGTCACATCACTGGTGGAGACTTGTACGGT<br>ATTGTATTTGAAAGCTTCGACAGGCTCCGTGAAGTTTTGC<br>AGTGATTTTCTCCCCTTAAATCGTCGAAAATGGCCCTCAA<br>TTCAGGTCTAAGTGCGAAACAAGATGCGCTCGAGCATGTA<br>ATGGCAGTATCGAGAGACTTTTCAAGAGGATCCCAAACTT<br>TAATGAAGAGTCGTCTGAAAGGAGCACAGAATGGCCACAG<br>TTTACTCAAGAAAAAAGCGGACGCCCTGCAGATGCGATTC<br>AGGATGATTCTAGGAAAAATTATTGAGACGACAAATTAGG<br>CGTCATTCCAATCCTAGCAGATATTCTCAGTGACTCTGTG | 5 |

TABLE 1-continued dsRNA constructs

| Whitefly gene target(s) | Sequence | SEQ ID NO: |
| --- | --- | --- |
| chain (Bta07573)-V-type proton ATPase subunit D1 (Bta00691)-V-type proton ATPase subunit H (Bta15084) | AAAGAAAAAGTTACCCGCATCATCTTGGCTGTATTCAGAA<br>ACTTAATCGAAAAACCAGAAGAGCCGAACATTGCAAAGGA | |
| Syntaxin 1A | GGAAACACAGCAGGCAAAACAAACTCTAGCAGATATTGAA<br>GCAAGACATGCGGATATTATAAAATTAGAAAATTCTATAC<br>GAGAGTTGCATGACATGTTTATGGATATGGCTATGCTTGT<br>TGAAAACCAGGGAGAAATGATTGACCGTATCGAATATCAT<br>GTAGAACATGCGGTCGATTATGTTCAAACTGCAACACAAG<br>ATACTAAGAAAGCATTAAAATATCAGAGTAAAGCGCGGC | 6 |
| Negative control (Watermelon Wun1) | ATGCGCCTCCTCACCGGCGCCTCCTCCTCCTTTGTCTTCG<br>CACCAATCTCTGTCGTCCCATTTGGGCCCAATTTCGTCCT<br>GGCGGAAGGCTACGACACAAAACGCGCCGTTTCCTGGGTC<br>CACGCCTGGACCATTACTGATGGGATCATCACCCACGTCA<br>AGGAATATCTCAACACCTCTGTTACTGTCAAGTGCTTCTC<br>CTCCGCCGCCGACGGGAACTCGCCTTCCGCATCTCCACCG<br>CCTAACTGCCAGAGTGTGTGGCAGAGCAAGGTCTGGGGAG<br>AATCGGTGGTGCCTGCTCTTGTTTTGGCTCTTTAG | 7 |
| Acetyl-cholines-terase 1 (Bta05381) | AAGGCAAAGTTCGAGGCACCACGCTCACCGCAGCAACAGG<br>CAAACAGGTCGATGCCTGGCTCGGCATACCTTACGCACAA<br>AAACCAATCGGGGCACTGCGGTTCCGGCACCCGCGGCCGA<br>TCGACAAGTGGGAGGGGATCCTGAACGCGACCAAGATGCC<br>CAACTCGTGCACGCAGATCGTGGATACGGTCTTCGGCGAC<br>TTCGCCGGCTCGGCCATGTGGAACCCGAACACGCCCATGT<br>CCGAGGACTGCCTCTACATCAACGTCATCACCCCGAAGCC<br>CCGGCCCCGCAACGCCGCCGTCATGGTCTGGATCTTCGGC<br>GGCGGCTTCTACACCGGGACGGCCACCCTCGACATCTACG<br>ACTACAAGATCCTCGCCTCCGAGGAGAACGTCATCCTCGT<br>CTCCATGCAGTACCGCATCACCTGCCTCGGCTTCCTCTAC<br>TTCGACACCCAGGACGTCCCCGGCAACGCGGGGCTCTTCG<br>ACCAGTTGATGGCCCTCCAGTGGATCAGGA | 8 |
| Cathepsin D | AACTCCTCCTCAGAATTTTAAGGTTGTTTTCGATACTGGA<br>TCCTCTAACCTTTGGGTGCCCTCCAAAAAGTGTAGCATCA<br>CCAACATAGCATGTTTGACTCACAGCAAATACAACAGCAA<br>AGCCTCCTCCACCTATGTAGCTAATGGCACAAAATTCCAT<br>ATTGCTTACGGATCTGGTAGTCTCAGTGGATTTCTCTCTA<br>CAGATACTGTTTCGATTGCTGGGTTATCTATTGTAAACCA<br>AACATTTGCAGAAGCTGTGACAGAACCAGGTCTAATTTTT<br>GTAATGGCTAAGTTTGATGGTATC<br>CTAGGACTTGGATATGATACAATCTCTGTTGATGGTGTTG<br>TTCCTCCCATCTACAAAATGTACCAGCAAGGTTTAATTGA<br>CGCACCAGTTTTCTCATTTTATCTAAACAGAAACACATCG<br>ACTCAGCCAGGTGGTGAGATTATTTTTGGTGGCTCAGATA<br>GTGAAAAGTACAAGGGTGACTTCACTTATGTACCTGTAAC<br>CAAAGAAGGATATTGGCAGTTCACCA | 9 |
| Heat shock protein 90 (Bta08575) (Bta01899) | AAGAAGAATAACATCAAGTTGTACGTCAGACGAGTATTCA<br>TCATGGACAATTGCGAAGATCTCATACCTGAGTATCTGAA<br>CTTTATCAAGGGGGTTGTTGATAGTGAAGATTTGCCTTTG<br>AACATCTCTCGAGAAATGTTACAGCAGAACAAAATTTTGA<br>AAGTGATTCGCAAAAACTTGGTCAAGAAATGTCTTGAATT<br>ATTTGAAGAGTTAGCAGAAGACAAAGAAAACTACCAAAAA<br>TTCTACGAGCAATTTAGCAAGAACCTGAAATTGGGCATGC<br>ACGAAGATACGCAAAATAGGAAGAAATTGTCAGATTTGCT<br>TCGTTACCAGACATCTGCCAGACTTCAGCCACTGGAGACG<br>ATGTCTGCTCATTTAAAGATTATGTAGCTCGTATGAAAGA<br>GAACCAGAAGCATATCTACTACATCACTGGTGAAAGCAAA<br>GATCAAGTAGCTAACTCCTCATTTGTCGAGCGAGTCAAGA | 10 |

TABLE 1-continued

| dsRNA constructs | | |
|---|---|---|
| Whitefly gene target(s) | Sequence | SEQ ID NO: |
| | AACGCGGTTTTGAAGTAATCTACATGACCGAACCCATCGA TGAATATGTAGTCCAGCAAATGAAAGACTACGATGGTAAG AACCTGGTCTCAGTCACGAAAGAAGGATTAGAACTGCCTG AGGACGAAGAAGAAAAGAAGAAATACGAGGAAGACAAAGT TAAGTTCGAAACCCTCTGCAAGG | |

The dsRNA of SEQ ID NO:1 was designed to target a single whitefly gene, flightin (Bta04605). The flightin gene is found in *Drosophila* indirect flight muscle. A null mutation of the flightin gene in *Drosophila* has previously been shown to result in loss of flight (Reedy et al, J. Cell. Biol., (2000) 151:1483-1500; Vigoreaux et al, J. Exp. Biol., (1998) 201:2033-44.

The dsRNA of SEQ ID NO:2 targets the whitefly gene Bta03986, a mediator of RNA polymerase II transcription subunit 7. The protein is a component of the mediator complex, a coactivator involved in the regulated transcription of nearly all RNA polymerase II-dependent genes (Zhang et al, Mol. Cell. (2005) 19:89-100). The mediator is recruited by promoters through direct interactions with regulatory proteins and convey a message for the assembly of a complex with RNA polymerase II and the general transcription factors (Zhang et al, supra).

The dsRNA of SEQ ID NO: 3 is a construct designed based on three whitefly genes: aquaporin (Bta01973) (nucleotides 1-150 of SEQ ID NO: 3), alpha-glucosidase (Bta11979) (nucleotides 151-350 of SEQ ID NO: 3), and trehalase (Bta12860) (nucleotides 351-778 of SEQ ID NO: 3). Aquaporins belong to a major intrinsic protein family that selectively transport water across the cell membranes and are integral parts of the cell membrane (Agre et al, Am. J. Physiol. (1993) 265:F463-76; Takata et al, Prog. Histochem. Cytochem. (2004) 39:1-83). Alpha-glucosidase is involved in carbohydrate metabolic processes that hydrolyse the glycosidic bond between two or more carbohydrates, or between a carbohydrate and a non-carbohydrate moiety. Alpha-glucosidase is essential for the degradation of glycogen to glucose in lysosomes (Brown & Brown, Biochem. Biophys. Acta (1970) 110:124-33). Like alpha-glucosidase, trehalase is also involved in carbohydrate metabolism, responsible for the degradation of the disaccharide alpha, alpha-trehalose into two glucose subunits (Kopp et al, J. Biol. Chem. (1993) 268:4766-74).

The dsRNA of SEQ ID NO: 4 targets the whitefly gene Bta02325, or cadherin-23. Cadherins are a class of transmembrane proteins and are the major adhesion molecules which mediate cell-cell adhesion through their extracellular domain and their cytosolic domains connect to the actin cytoskeleton by binding to catenins (Brieher & Yap, Curr. Opin. Cell Biol., (2013) 25:39-46; Guan et al, PLoS One (2014) 9:e102153).

The dsRNA of SEQ ID NO: 5 is a concatemer that was designed based on four genes encoding vacuolar ATPases (v-ATPase) from whitefly: v-ATPase-A (Bta08447) (nucleotides 1-133 of SEQ ID NO: 5), v-ATPase-B (Bta07573) (nucleotides 134-260 of SEQ ID NO: 5), v-ATPase-D (Bta00691) (nucleotides 261-390 of SEQ ID NO: 5), and v-ATPase-H (Bta15084) (nucleotides 1-150 of SEQ ID NO: 5). The v-ATPases are ATP-driven proton pumps that function to acidify intracellular compartments and transport protons across the plasma membrane. V-ATPases are evolutionarily conserved enzymes found in intracellular membranes and plasma membranes of eukaryotic organisms. V-ATPase unit consists of nine polypeptides from A through H. Their housekeeping functions include acidifying endosomes, lysosomes, phagosomes, compartments for uncoupling receptors and ligands, autophagosomes, and elements of the golgi apparatus (Forgac, M., Nature Ref. Mol. Cell Biol., (2007) 8:917-29).

The dsRNA of SEQ ID NO: 6 targets the whitefly syntaxin 1A gene, Syntaxins are membrane associated proteins involved in calcium regulated exocytosis and have been implicated in docking of synaptic vesicles with the plasma membrane (Woodbury and Rognlien, Cell Biol. Intl, (2000) 24: 809-818; Lam et al., Mol. Biol. Cell (2008)19: 485-497). Syntaxin 1A (STX1A) is important in ion channel regulation and is critical for functioning of the insect nervous system.

The dsRNA of SEQ ID NO: 7, targets a portion of Cla008106, a gene from watermelon (*Citrullus lanatus*), encoding Wun1-Wound-induced protein. This dsRNA was designed because it has no significant homology to any genes within the whitefly genome and, therefore, is an appropriate negative control construct for experiments targeting whitefly genes.

The dsRNA of SEQ ID NO: 8 targets the whitefly acetylcholine esterase 1 gene. Acetylcholinesterase is an enzyme that catalyzes the breakdown of acetylcholine and of some other choline esters that function as neurotransmitters. They are inhibited by organophosphate and carbamate insecticides compound (Hartmann et al, J. Neurochem., (2007) 100:1421-9; Girard et al, Life Sci., (2007) 80:2380-5). Acetylcholinesterase (AChE) plays an important role in the cholinergic synapses and neuromuscular junctions of both invertebrates and vertebrates (Toutant et al, J. Neurochem., (1988) 50:209-18). In addition to its neuronal function, AChE has been elucidated to play non-neuronal roles, including neurite outgrowth, synapse formation (Olivera et al, Mol. Cell. Neurosci., (2003) 23:96-106), glia activation modulation, tau phosphorylation (Ballard et al, Curr. Alzheimer Res., (2005) 2:307-18), and xenobiotic defense (Kim et al, Insect Biochem Mol Biol., (2014) 48:75-82).

The dsRNA of SEQ ID NO:9 targets the whitefly cathepsin D gene. Cathepsins are proteases that have wide biological implications including their involvement in protein degradation, apoptosis, as well as signaling, and their activity in the late endosome and lysosome has been widely implicated in virus transmission (Kubo et al, Adv. Virol., (2012) 2012:640894; Sim et al, PLoS Pathol., (2012) 8:e10002631; Pinheiro et al, Mol. Cell. Proteom., (2016) 4 suppl. 1:S230-S243).

The dsRNA of SEQ ID NO: 11 targets the whitefly heat shock protein 90 gene. Heat shock protein 90 (Hsp90) is a molecular chaperone required for the stability and function of a number of signaling proteins and is also involved in protein folding (Neckers & Ivy, Curr. Opin. Oncol., (2003) 15:419-24). The expression of Hsp90 was up-regulated with the rise of temperature in *Grapholita molesta* (Chen et al, Insect Sci., (2014) 21:439-48). This dsRNA is a concatemer with sequences from two genomic regions: Bta08575 (nucleotides 1-339) and Bta01899 (nucleotides 400-666).

Having described the invention in general, below are examples illustrating the generation and efficacy of the invention. Neither the examples, nor the general description above should be construed as limiting the scope of the invention.

EXAMPLES

Example 1 dsRNA Synthesis

Total RNA was extracted from adult whiteflies (*B. tabaci* MEAM1) using TRIzol (Invitrogen, USA) followed by the Direct-zol RNA MiniPrep kit (Zymo Research Corporation, USA) following the manufacturers' instructions as previously described (Kaur et al, BMC Genomics (2017) 18:370). cDNA was prepared using iScript™ cDNA Synthesis Kit (Bio-Rad, USA). dsRNA constructs were synthesized at USDA-ARS, Salinas, Calif. using T7 polymerase promoters attached to 5' ends of each of forward and reverse primers using the MEGAscript RNAi Kit (ThermoFisher Scientific, USA), or were synthesized commercially by Genolution Inc., South Korea. All dsRNA species, and the genes to which they are targeted, are listed in Table 1.

Example 2

Feeding Assay

*Bemisia tabaci*, MEAM1 (biotype B) adults were exposed to dsRNA incorporated into 70 ul of artificial diet at 40 ng/ul for a period of up to 7 days (Upadhyay et al., 2011). Diet contained 20% sucrose with pH=7. Twenty adult whiteflies were allowed to feed on the diet containing dsRNA layered in between two UV-sterilized pieces of Parafilm stretched across the top of a glass vial. Whiteflies fed on diets containing dsRNA were incubated at 25° C. and 16 h Light: 8 h Dark photoperiod in a controlled chamber. A negative control assay with diet only (20% sucrose) and a second negative control consisting of 20% sucrose diet containing dsRNA directed against a watermelon gene (SEQ ID NO:7) at the same concentration as the dsRNA test constructs were included in assay. Efficacy of each dsRNA was tested with three biological replications with three technical replications per construct.

Figure 1B:
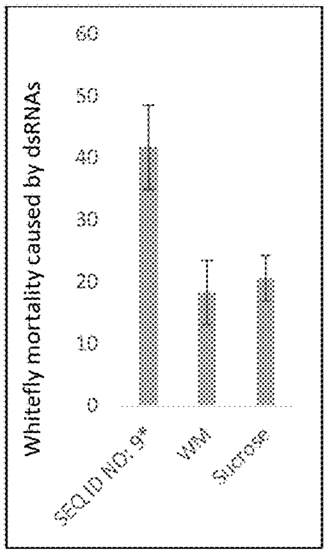
Figure 1C:
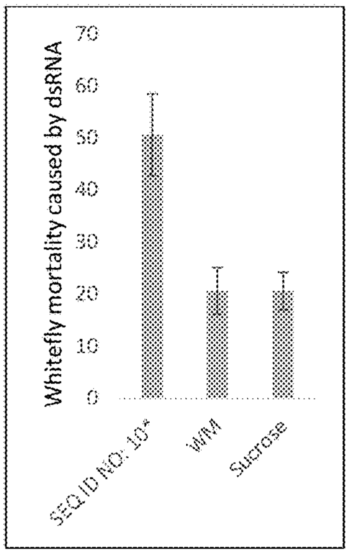
Figure 1D:
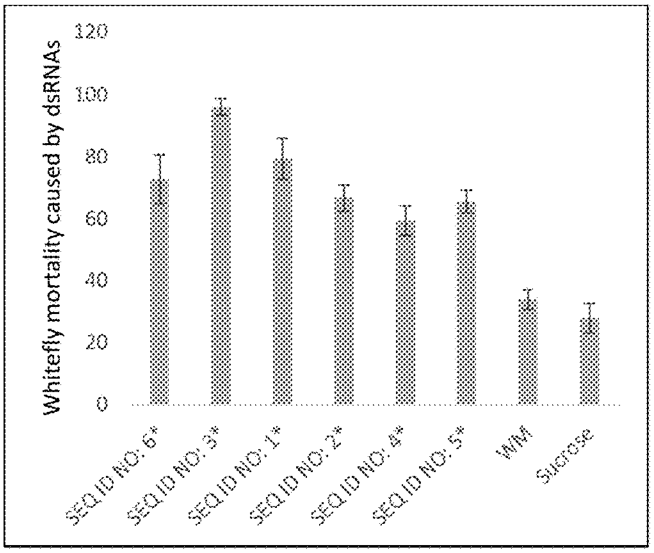

The dsRNA construct designed to target flightin (SEQ ID NO: 1) showed a mortality rate of 79.4±6.6 percent (p value<0.0001) compared to negative controls: WM with 33.9±3.2 and sucrose only with 27.8±4.7 mortality rates (FIG. 1D). The dsRNA construct designed to target Bta03986 (SEQ ID NO: 2) caused whitefly mortality rate of 66.7±4.2 percent (p value<0.0001) (FIG. 1D). The dsRNA concatemer designed to target aquaporin, alpha-glucosidase and trehalase (SEQ ID NO: 3) showed the highest mortality rate of 96.1±2.7 percent (p value<0.0001) compared to negative controls: WM with 33.9±3.2 and sucrose with 27.8±4.7 mortalities (FIG. 1D). The dsRNA construct targeting cadherin-23 (SEQ ID NO: 4) showed a mortality rate of 59.4±4.8 percent (p value<0.0001) compared to negative controls: WM with 33.9±3.2 and sucrose with 27.8±4.7 mortalities (FIG. 1D). The dsRNA concatemer containing sequences intended to target multiple subunits of v-ATPase (SEQ ID NO: 5) showed a mortality rate of 65.6±3.7 percent (p value<0.0001) compared to negative controls: WM with 33.9±3.2 and sucrose with 27.8±4.7 mortalities (FIG. 1D). The dsRNA construct targeting Syntaxin 1A (SEQ ID NO: 6) showed a mortality rate of 72.8±7.8 percent (p value<0.0008) (FIG. 1D). The dsRNA construct targeting Acetylcholinesterase (SEQ ID NO: 8) showed a mortality rate of 51.1±6.7 percent (p value<0.0003) (FIG. 1A). The dsRNA construct targeting Cathepsin D (SEQ ID NO: 9) showed a mortality rate of 41.7±6.8 percent (p value<0.0022) (FIG. 1B). The dsRNA construct targeting heat shock protein 90 (SEQ ID NO: 10) showed a mortality rate of 50.6±7.9 percent (p value<0.0011) (FIG. 1C).

Example 3

Canonical and Non-Canonical dsRNA Comparisons

Canonical dsRNA was synthesized using the Ambion® MEGAscript® RNAi Kit Transcription and RNAi Preparation, and 2'-F cytosine and uracil modified non-canonical dsRNA was synthesized using the Lucigen® DuraScribe® T7 Transcription Kit, per manual instructions. Noncanonical sequences substituted uracil at all threonine residues and 2'-F cytosine at all cytosine residues in SEQ ID NO: 6.

Studies were conducted to evaluate performance of canonical and non-canonical dsRNA constructs targeting a selective area of the gene targeted by construct SEQ ID NO: 6 in the whitefly *Bemisia tabaci* MEAM1. This was to clarify the performance of different dsRNA orientations for induction of whitefly mortality, and can be applied using topical application or delivery via agroinfiltration. The dsRNA was delivered to tomato seedlings through traditional uptake methods, with cut stems allowed to uptake dsRNA in water after which plants were provided with water and later rooting solution to facilitate rooting of plantlets. Three days following uptake of dsRNA (to allow distribution of dsRNA throughout plants), 25 adult whiteflies per plant were allowed to feed on cuttings for 10 days.

Figure 2:
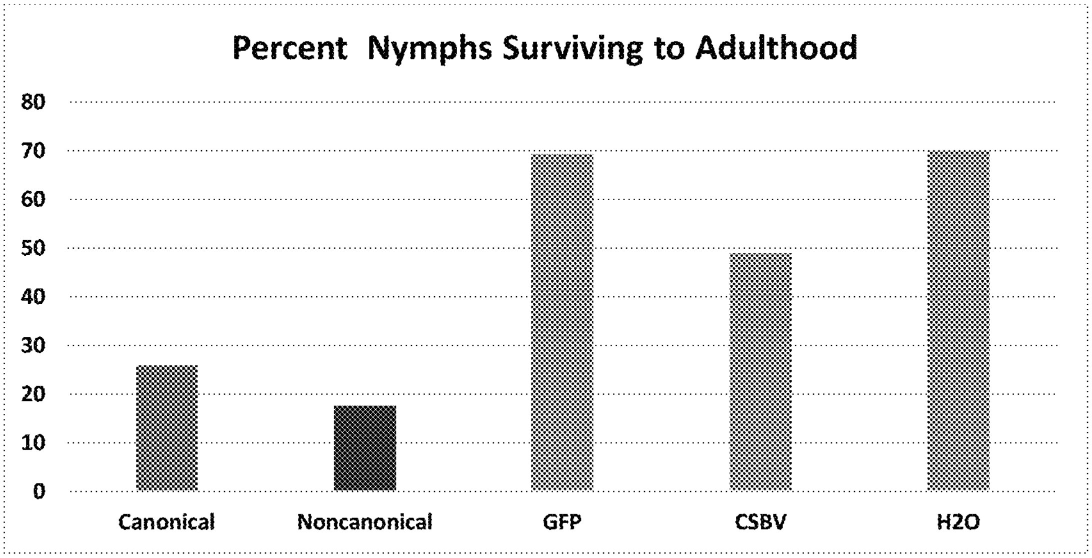
FIG. 2 provides a graphic representation of data comparing the effects of canonical and non-canonical dsRNA (SEQ ID NO: 6) sequences on whitefly mortality.

Upon completion of initial mortality tests, whitefly mortality was determined, and the number of eggs and nymphs was determined for each plant (2-4 true leaves). Rooted tomato seedlings were subsequently transferred to soil in 4-inch diameter pots and placed in insect-proof ventilated bioassay cages (1 cage per plant). Whitefly emergence was determined for each construct. Each experiment included five treatments×10 replications, with each replication composed of an individual tomato seedling. The assay compared numbers of whiteflies that emerged as adults on rooted plants compared with the number of nymphs present on plants at the time of planting among five treatments (canonical SEQ ID NO: 6, non-canonical SEQ ID NO: 6, GFP negative control, CSBV negative control, and water). Results demonstrated only 17.7% of whiteflies survived to develop into adults by 9 days post-planting (end of experiment due to plant size) for those treated with the non-canonical construct (FIG. 2). This means there was 82.3% whitefly mortality among developing nymphs for the non-canonical SEQ ID No: 6 construct. Similarly, only 25.9% of whiteflies developed to adulthood on plants treated with the canonical SEQ ID NO: 6 construct, indicating 74.1% mortality. Controls were found to have much higher levels of survival (much lower mortality) with 49 to 70 percent of whiteflies in the negative control treatments surviving to maturity.

A similar study was conducted in which canonical and noncanonical sequences of SEQ ID NO: 6 were compared on okra seedlings. In those experiments, okra seedlings approximately 2 inches in height with two true leaves were transplanted into 50 mL conical tubes. Soil was allowed to dry for approximately 72 hours, after which dsRNA (40 ug/10 ml water) was used to drench soil in which seedlings were planted. Seedlings were allowed to absorb dsRNA for 48 hours. Approximately 25 whiteflies were then added to each seedling which was covered with a ventilated bioassay tube, and the experiment was allowed to run for 8 days, at ambient room temperature, with a 16 h:8 h light/dark period. Three whiteflies were collected from each tube on day 7 and processed for RNA to quantify gene expression through RT-qPCR.

Figure 3:
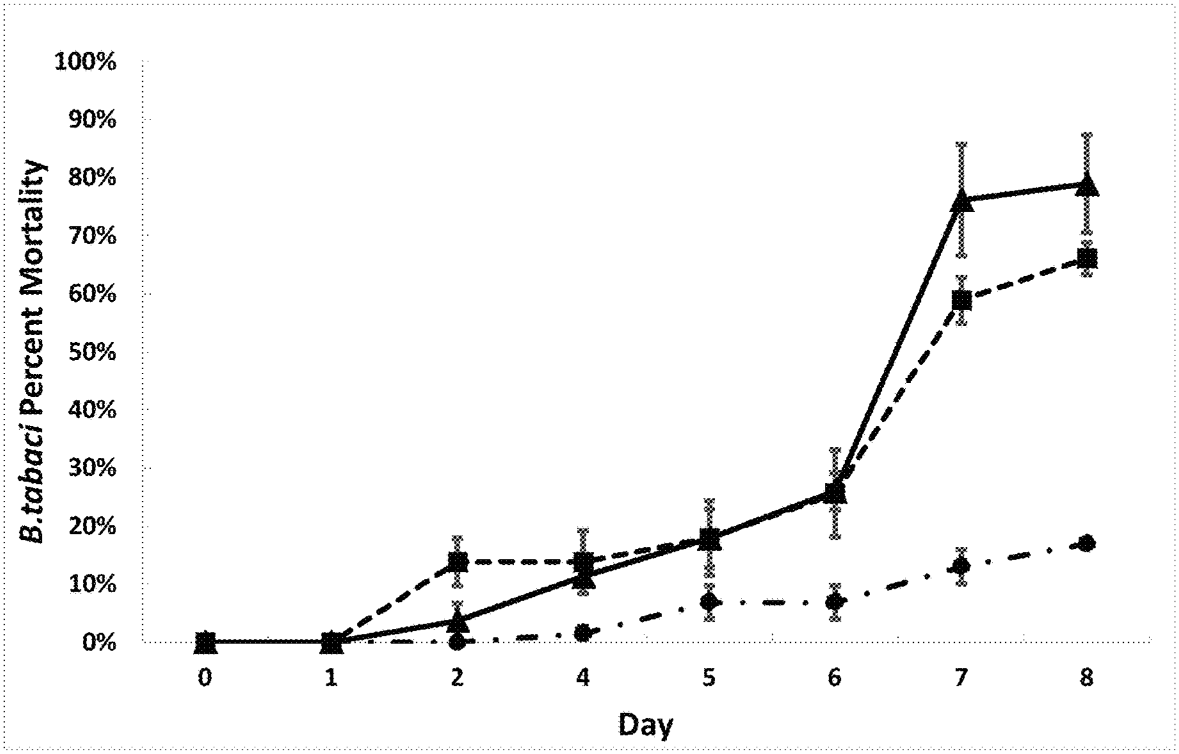
FIG. 3 provides graphic representation of data showing increased mortality of *B. tabaci* on okra plants. Mortality was significantly higher in both canonical (filled squares) and non-canonical (filled triangles) SEQ ID NO: 6 treatment groups compared to irrelevant control dsRNA (GFP, filled circles). A one-way ANOVA was performed on the percentage of dead whiteflies in each treatment group on day 8. The ANOVA indicates statistical significance among treatment groups with a p-value of 0.004 ($\alpha$=0.05). Error bars represent the standard error of three biological replicates.
Figure 4:
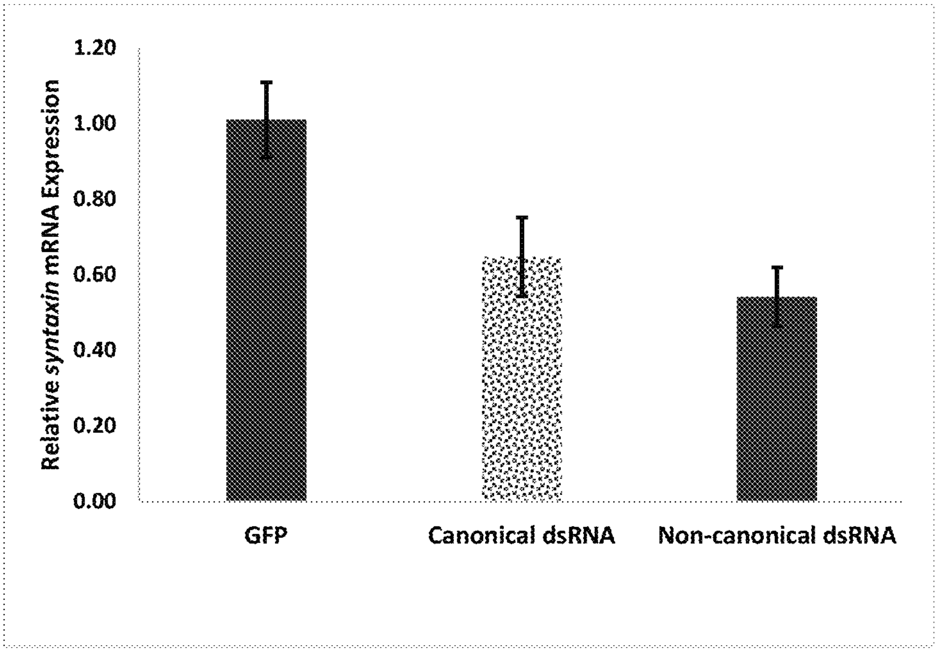
FIG. 4 provides graphic representation of decrease in gene expression in *B. tabaci* exposed to canonical and non-canonical dsRNA (SEQ ID NO: 6) as determined by qPCR.

Mortality results at 8 days demonstrated that adult mortality was 62% higher on okra plants treated with non-canonical dsRNA and 49% higher in okra treated with canonical dsRNA, when compared to the control treatments (FIG. 3). Both canonical and non-canonical dsRNA resulted in down-regulation of the mRNA for the gene encoded by SEQ ID NO: 6 in *B. tabaci* (FIG. 4), and relative expression of the targeted mRNA was reduced 1.6-fold and 1.9-fold when treated with canonical and non-canonical dsRNA, respectively. A one-way ANOVA was performed on relative expression values of mRNA across all treatment groups. The ANOVA indicated statistical significance between the GFP control and dsRNA treatments with a p-value of 0.03 ($\alpha$=0.05). Relative mRNA expression does not appear to be significantly different between canonical and non-canonical dsRNA treatments. Error bars represent the standard error of three biological replicates each with three technical replicates.

Example 4

Effects of dsRNA Via Agroinfiltration

Figure 5:
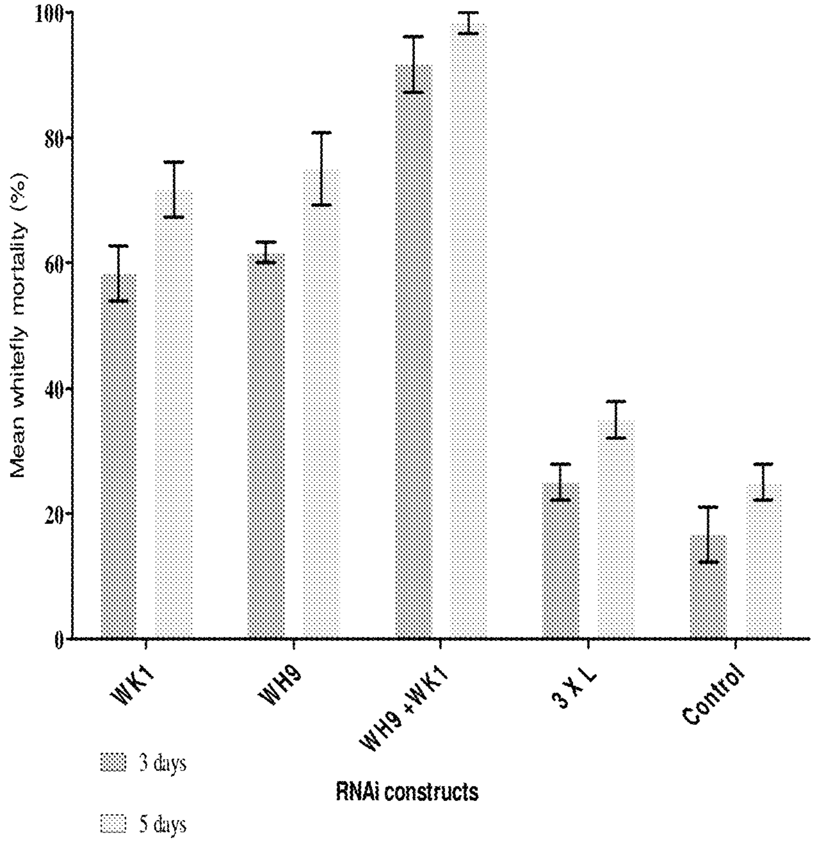
FIG. 5 provides graphic representation of data from a transient assay for testing efficacy of RNAi constructs for control of cassava super-abundant whiteflies (*B. tabaci* SSA-SG1). Mortality of whiteflies (Number of dead whiteflies/Total number of whiteflies inoculated as percent) was recorded on cassava leaves agroinfiltrated with pUSVL3xL-WK1 (SEQ ID NO: 3), pUSVL3xL-WH9 (SEQ ID NO: 6), pUSVL3xL-WK1+pUSVL3xL-WH9 (SEQ ID NO: 3 and SEQ ID NO: 6), empty plasmid (3XL) and mock infiltrated (MES buffer) leaves (control). Data is represented as mean of three replicates and standard error.

The combined effect of two simultaneously agroinfiltrated constructs was tested in cassava leaves through transient expression of agroinfiltrated SEQ ID NO: 6+SEQ ID NO: 3 ("pUSVL3xL-WH9"+"pUSVL3xL-WK1") together as compared with agroinfiltrated SEQ ID NO: 6 (pUSVL3xL-WH9) and SEQ ID NO: 3 (pUSVL3xL-WK1) individually, as well as control constructs (FIG. 5). All agroinfiltration plasmids were constructed using standard protocols and contained the indicated dsRNA constructs inserted between the T-DNA borders of the *Agrobacterium* vector, pUSVL3xL (a modified version of pCAMBIA 2300 (www.snapgene.com/resources/plasmid-files/?set=plant_vectors&plasmid=pCAMBIA2300) containing a triple left border sequence (Kuraya et al, Mol. Breeding, (2004) 14:309-20)). Agroinfiltration was accomplised using standard protocols (Diaz et al, Rev. MVZ Cordoba, (2014) 19:4338-49). *Agrobacterium* harboring individual constructs were cultured to 0.25 optical densities ($0.D^{600}$) in MES buffer. To evaluate potential synergistic effects of SEQ ID NO: 6 and SEQ ID NO: 3 together, an equal volume of 0.25 $O.D^{600}$ of each of the *agrobacterium* suspensions were mixed in a falcon tube in preparation for infiltration. Thereafter TMS 98/0505 cassava leaves were agroinfiltrated and twenty adult whiteflies (2-3 days old) were attached in clip cages onto agroinfiltrated cassava leaves 48 hrs post-infiltration. Three cassava leaves of each plant of 3 replicates were agroinfiltrated for each target construct. The mortality of whiteflies was monitored daily and a count of live adults taken on the $3^{rd}$ and $5^{th}$ day post challenge of the agroinfiltrated leaves. The experiment was repeated three times. The results revealed a significant difference in mortality of whiteflies fed on agroinfiltrated cassava leaves and control non-treated cassava leaves infiltrated with MES buffer (FIG. 5, representative data from one experiment is shown).

Figure 6:
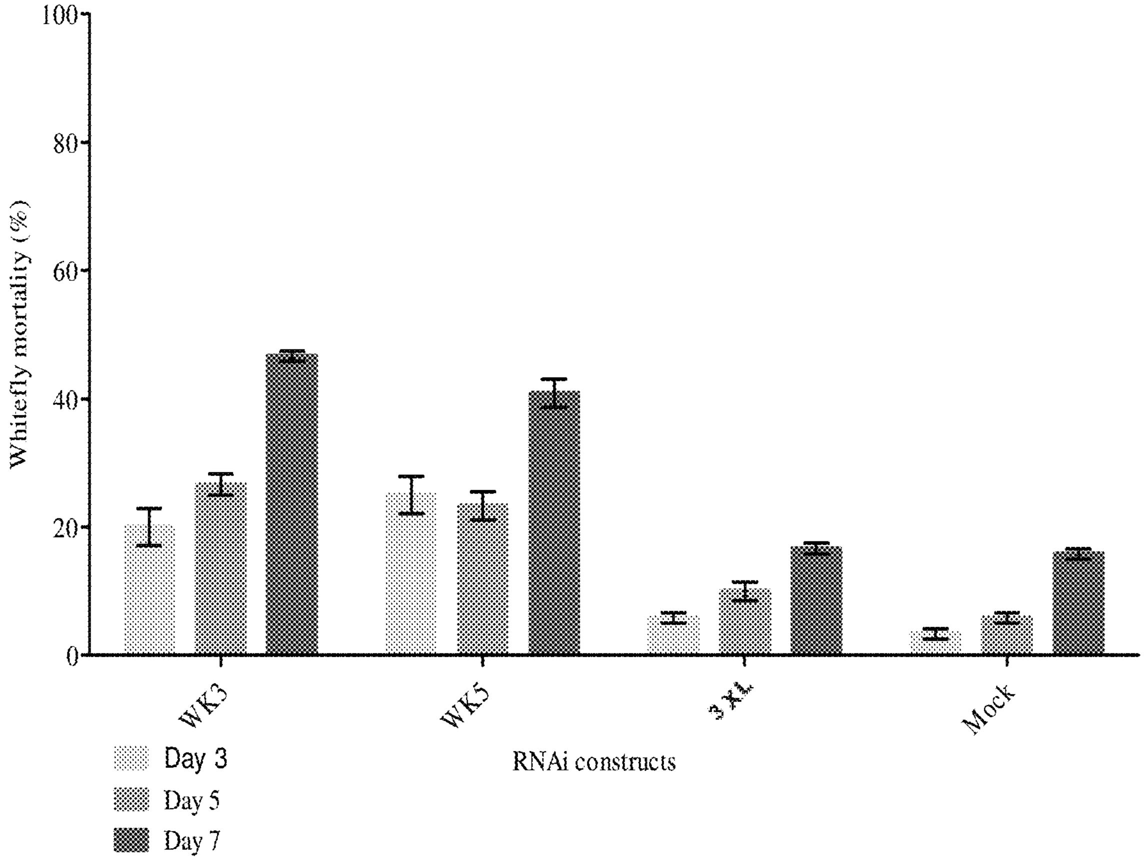
FIG. 6 provides Transient assay for testing efficacy of RNAi constructs for control of whiteflies (*B. tabaci* SSA-SG1). Mortality (%) of whiteflies (Number of dead whiteflies/Total number of whiteflies inoculated×100) was recorded on cassava leaves agroinfiltrated with different RNAi constructs (SEQ ID NO: 2 (pUSVL3xL-WK3) or SEQ ID NO: 5 (pUSVL3xL-WK5)), empty plasmid (3XL) and mock infiltrated (MES buffer) leaves (control). Data is represented as mean of three replicates and standard error.

RNAi-inducing constructs pUSVL3xL-WK3 (containing SEQ ID NO: 2) and pUSVL3xL-WK5 (containing SEQ ID NO: 5), which contain dsRNA constructs inserted between the T-DNA borders of the *Agrobacterium* vector, pUSVL3xL, were agroinfiltrated into cassava leaves of TMS 98/0505 plants to test their effect on mortality of whiteflies. Twenty adult whiteflies (2-3 days old) were clip caged onto agroinfiltrated cassava leaves two days post agroinfiltration. Three cassava leaves of each plant of 3 replicates were agroinfiltrated with each target construct. The mortality of whiteflies was monitored daily and live adults were counted on 3rd, $5^{th}$ and $7^{th}$ day post challenge of the agroinfiltrated leaves. These results revealed a significant difference in mortality of whiteflies fed on agroinfiltrated cassava leaves in comparison to control non-treated cassava leaves mock infiltrated with MES buffer (FIG. 6). The empty plasmid was also used as a control.

Figure 7:
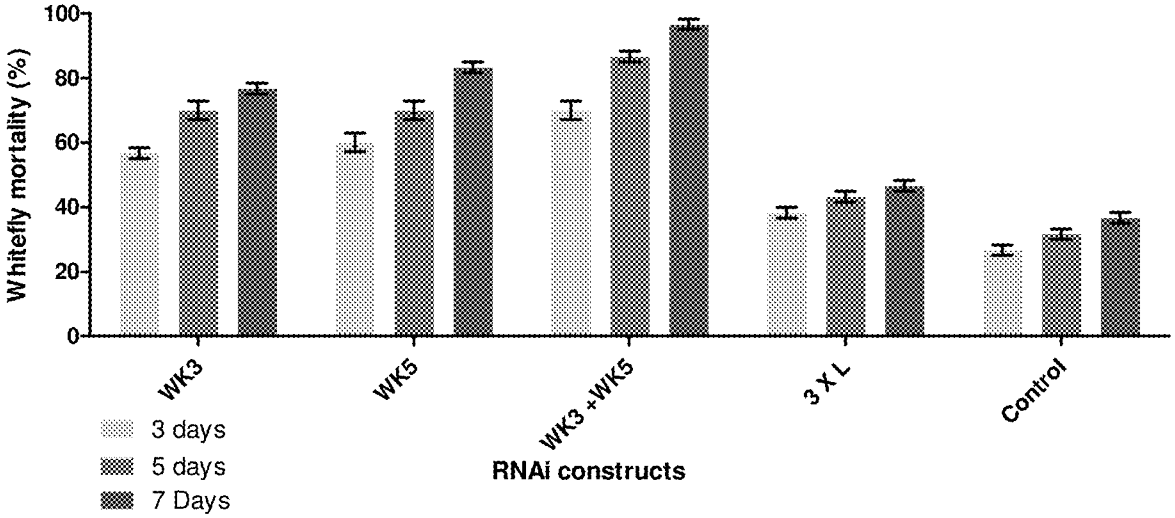
FIG. 7 provides graphic representation of data from RNAi induction and mortality cause by *agrobacterium*-expressed dsRNAs (transient assay). Mortality (%) of whiteflies (Number of dead whiteflies/Total number of whiteflies inoculated×100) was recorded on cassava leaves agroinfiltrated with different RNAi constructs (SEQ ID NO: 2 (pUSVL3xL-WK3), SEQ ID NO: 5 (pUSVL3xL-WK5)), a combination of both of these constructs, empty plasmid (3XL) and mock infiltrated (MES buffer) leaves (control). Data is represented as mean of three replicates and standard error.

The potential for a combined effect of these two RNAi constructs was tested through transient expression of SEQ ID NO: 2+SEQ ID NO: 5 (pUSVL3xL-WK3+pUSVL3xL-WK5) constructs along with individual SEQ ID NO: 2 ((pUSVL3xL-WK3) or SEQ ID NO: 5 (pUSVL3xL-WK5) and control constructs in cassava leaves (FIG. 7). For these experiments, *Agrobacterium* harboring each construct were grown separately to obtain optical densities ($O.D^{600}$) of 0.25. For synergistic effect of SEQ ID NO: 2+SEQ ID NO: 5 at equal volumes of 0.25 O. $D^{600}$ cultures were mixed in a falcon tube in preparation for infiltration. Thereafter, cassava leaves of TMS 98/0505 were agroinfiltrated and twenty adult whiteflies (2-3 days old) were attached onto the underside of agroinfiltrated cassava leaves 48 hrs. post infiltration in clip-cages. Three cassava leaves of each plant of 3 replicates were agroinfiltrated for each target construct. The mortality of whiteflies was monitored daily and live adults were counted on the $3^{rd}$, $5^{th}$ and $7^{th}$ day post challenge of the agroinfiltrated leaves. As expected, this experiment confirmed significant differences in mortality of whiteflies fed agroinfiltrated cassava leaves in comparison to non-treated control cassava leaves infiltrated with MES buffer only.

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A double-stranded ribonucleic acid (dsRNA) comprising a first strand comprising a sequence with at least 75% complementarity to the full length of SEQ ID NO: 3 and a second strand complementary to the first strand.

2. The dsRNA of claim 1, wherein the first strand has at least 95% sequence complementarity to the full length of SEQ ID NO: 3.

3. The dsRNA of claim 1 or claim 2, wherein the second strand comprises SEQ ID NO: 3.

4. The dsRNA of claim 1 or claim 2, wherein the dsRNA is capable of inducing ribonucleic acid interference (RNAi) when ingested by an insect.

5. The dsRNA of claim 4, wherein the insect is *Bemisia tabaci.*

6. A DNA molecule comprising a promoter functional in a host cell and a heterologous DNA encoding a dsRNA comprising a first strand and a second strand, wherein the first strand comprises a sense region with at least 75% sequence complementarity to the full length of SEQ ID NO: 3 and a second strand complementary to the first strand.

7. The DNA molecule of claim 6, wherein the host cell is a plant cell.

* * * * *